United States Patent
Van Gompel et al.

(10) Patent No.: US 9,662,248 B2
(45) Date of Patent: May 30, 2017

(54) SELECTIVE MODIFICATION OF A NONWOVEN SURFACE

(75) Inventors: Paul T. Van Gompel, Hortonville, WI (US); Yung H. Huang, Appleton, WI (US); Gregory K. Hall, Menasha, WI (US); Cedric A. Dunkerly, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 703 days.

(21) Appl. No.: 13/289,143

(22) Filed: Nov. 4, 2011

(65) Prior Publication Data

US 2012/0053552 A1 Mar. 1, 2012

Related U.S. Application Data

(63) Continuation of application No. 10/837,155, filed on Apr. 30, 2004, now Pat. No. 8,562,580.

(51) Int. Cl.
*A61F 13/62* (2006.01)
*A61F 13/15* (2006.01)

(52) U.S. Cl.
CPC ...... *A61F 13/15203* (2013.01); *A61F 13/627* (2013.01); *Y10T 24/27* (2015.01); *Y10T 24/2783* (2015.01)

(58) Field of Classification Search
USPC .............................. 604/391; 24/306, 442–452
See application file for complete search history.

(56) References Cited

U.S. PATENT DOCUMENTS

| | | | |
|---|---|---|---|
| 3,694,867 A * | 10/1972 | Stumpf | 24/448 |
| 4,076,663 A | 2/1978 | Masuda et al. | |
| 4,286,082 A | 8/1981 | Tsubakimoto et al. | |
| 4,340,563 A | 7/1982 | Appel et al. | |
| 4,725,473 A | 2/1988 | Van Gompel et al. | |
| 4,798,603 A | 1/1989 | Meyer et al. | |
| 4,973,326 A | 11/1990 | Wood et al. | |
| 5,019,073 A | 5/1991 | Roessler et al. | |
| 5,106,383 A | 4/1992 | Mulder et al. | |
| 5,226,992 A | 7/1993 | Morman | |
| 5,407,722 A | 4/1995 | Peake, III et al. | |
| 5,449,530 A | 9/1995 | Peake, III et al. | |
| 5,476,702 A | 12/1995 | Datta et al. | |
| 5,554,239 A | 9/1996 | Datta et al. | |
| 5,586,371 A | 12/1996 | Thomas | |
| 5,605,735 A | 2/1997 | Zehner et al. | |
| 5,624,429 A | 4/1997 | Long et al. | |
| 5,647,864 A | 7/1997 | Allen et al. | |
| 5,762,645 A * | 6/1998 | Peck et al. | 604/391 |
| 5,858,515 A | 1/1999 | Stokes et al. | |
| 5,997,981 A | 12/1999 | McCormack et al. | |
| 6,030,373 A | 2/2000 | Vangompel et al. | |
| 6,264,641 B1 | 7/2001 | Van Gompel et al. | |

(Continued)

FOREIGN PATENT DOCUMENTS

| EP | 0 539 703 B1 | 3/1997 |
|---|---|---|
| JP | 07-213310 A | 8/1995 |

(Continued)

*Primary Examiner* — Peter S Vasat
(74) *Attorney, Agent, or Firm* — Kimberly-Clark Worldwide, Inc.

(57) ABSTRACT

Improved fastening systems are described. More particularly, improved fastening systems for disposable absorbent articles are described.

14 Claims, 5 Drawing Sheets

(56) References Cited

U.S. PATENT DOCUMENTS

| | | |
|---|---|---|
| 6,296,629 B1 | 10/2001 | Siebers et al. |
| 6,332,250 B1 | 12/2001 | Igaue et al. |
| 6,387,471 B1 | 5/2002 | Taylor et al. |
| 6,402,730 B1 | 6/2002 | Malowaniec |
| 6,849,142 B1 | 2/2005 | Goulait |
| 6,955,847 B1 * | 10/2005 | Itou et al. .................... 428/174 |
| 7,032,278 B2 | 4/2006 | Kurtz, Jr. |
| 2002/0026173 A1 | 2/2002 | Tani et al. |
| 2002/0099353 A1 | 7/2002 | Olson |
| 2002/0160143 A1 | 10/2002 | Shepard et al. |

FOREIGN PATENT DOCUMENTS

| | | |
|---|---|---|
| WO | WO 97/24482 A1 | 7/1997 |
| WO | WO 97/25893 A1 | 7/1997 |

* cited by examiner

SELECTIVE MODIFICATION OF A NONWOVEN SURFACE

This application is a continuation of, and claims priority to, application Ser. No. 10/837,155 filed on Apr. 30, 2004 now U.S. Pat. No. 8,562,580. The entirety of application Ser. No. 10/837,155 is hereby incorporated by reference.

BACKGROUND

The present invention relates to improved fastening systems. More particularly, the present invention related to improved fastening systems for disposable absorbent articles.

Conventional disposable absorbent articles, such as disposable diapers, have typically included a bodyside liner, an outer cover and an absorbent core disposed between the outer cover and the bodyside liner. The disposable absorbent articles have generally defined a front region, a rear region and a crotch region which extends between and connects the front and rear regions. Such conventional disposable absorbent articles have also included fastening systems which are configured to secure the article on the wearer's waist. The disposable absorbent articles have also been constructed with various types of elasticized portions at the waist and leg opening regions. Such elasticized portions have been used to reduce the leakage of body exudates from the disposable absorbent article and improve the appearance and fit of the article about the wearer.

Typically, the fastening systems on conventional disposable absorbent articles have included a pair of fasteners located on the outermost corners of the article in one of the waist regions. Such fasteners have been configured to releasably engage a complimentary fastener in the opposite waist region of the disposable absorbent article. For example the fastening systems have included a pair of mechanical fasteners, such as hook material, located on the outermost corners of the disposable absorbent article in the rear region of the article. Such systems have also included a complimentary fastener, such as a loop material panel, located on the outer surface of the outer cover of the disposable absorbent article in the front region of the article. In such a configuration, the disposable absorbent article has been positioned between the legs of the wearer and the hook material has been releasably attached to the loop material panel to secure the article about the waist of the wearer. In some disposable absorbent articles, the loop material panel has been removed, and the hook material has been releasably attached to the outer cover of the diaper, known as a fasten anywhere configuration.

However, conventional disposable absorbent articles which are configured as described above have exhibited several shortcomings. For example, with the desire for disposable absorbent articles to be more clothlike, manufacturers have made the outer cover and the loop material increasingly more fluffy, soft and correspondingly susceptible to abrasion. As a result, these clothlike materials become abraded upon disengagement of the mechanical fasteners. This abrasion may cause a decrease in aesthetic appeal, as well as a decrease in functionality of the attachment system.

As a result, there has remained a need for improved fastening systems. Moreover, there has remained a need for improved fastening systems for disposable absorbent articles.

SUMMARY

The present inventors undertook intensive research and development efforts concerning improving fastening systems. While conducting their research, the present inventors discovered unique methods of modifying fastening systems that resulted in improved fastening systems and thus well suited for use is disposable absorbent articles. One version of the present invention involves a fastening system suitable for incorporation into a disposable absorbent article, the fastening system having a male component having a plurality of hook elements and a female component adapted for releasable engagement with the male component. The female component comprises a web having a fibrous structure. The female component contains at least a first area and a second area, the first area being modified such that a peak shear force to disengage the male component from the first area is at least 10% less than a peak shear force to disengage the male component from the second area.

Another version of the present invention relates to an absorbent article having a fastening system. The fastening system having a male component having a plurality of hook elements and a female component adapted for releasable engagement with the male component. The female component comprises a web having a fibrous structure, wherein the female component contains at least a first area and a second area. The first area is modified such that a peak shear force to disengage the male component from the first area is at least 10% less than a peak shear force to disengage the male component from the second area.

Yet another version of the present invention involves a disposable absorbent article having an outer cover, a liner superposed over at least a portion of the outer cover, an absorbent core disposed between the liner and the outer cover and a fastening system. The fastening system having a male component having a plurality of hook elements and a female component adapted for releasable engagement with the male component. The female component having a fibrous structure and defining at least a first area and a second area. The peak shear force to disengage the male component from the first area is at least 10% less than the peak shear force to disengage the male component from the second area.

Also disclosed is a disposable absorbent article having an outer cover having a bodyfacing surface and a garment facing surface, a liner superposed over the bodyfacing surface of the outer cover, the outercover comprising an outer cover nonwoven web and an absorbent core disposed between the liner and the bodyfacing surface of the outer cover. The disposable absorbent article also has a fastening system. The fastening system comprises a male component having a plurality of hook elements and a female component adapted for releasable engagement with the male component. The female component comprises a web having a fibrous structure. The outer cover nonwoven web forms the female component. The female component contains at least a first area and a second area, where a peak shear force to disengage the male component from the first area is at least 10% less than a peak shear force to disengage the male component from the second area. The male component is located in a rear region of the disposable absorbent article, and the first area is located in a front region of the disposable absorbent article.

DRAWINGS

The foregoing and other features, aspects and advantages of the present invention will become better understood with regard to the following description, appended claims and accompanying drawings where:

DESCRIPTION

The present invention relates to improved fasteners, and improved fasteners for use in disposable absorbent articles. As used herein, the term "disposable" refers to articles which are intended to be discarded after a limited use and which are not intended to be laundered or otherwise restored for reuse. The disposable absorbent articles of the present invention will be described in terms of a disposable diaper which is adapted to be worn by infants about the lower torso. It is understood that the improved fastening system of the present invention is equally adaptable for use with other types of disposable absorbent articles such as adult incontinent garments, children's training pants, surgical gowns and the like.

With regard to the designated surfaces of a disposable absorbent article and its components, the various upper or bodyfacing surfaces are configured to face toward the body of the wearer when the disposable absorbent article is worn by the wearer for ordinary use. The various opposing, lower or garment facing surfaces are configured to face away from the wearer's body when the disposable absorbent article is worn by the wearer.

As used herein, reference to two materials or elements being "joined" is intended to refer to the situation wherein the two materials or elements are directly joined to one another or where they are indirectly joined to one another or where they are indirectly joined to an intermediate element. Similarly, methods of joining two materials or elements include forming the elements or materials integrally, or attaching the elements together such as through the use of adhesive bonds, sonic bonds, thermal bonds, pinning, stitching, or a variety of other attachment techniques known in the art, as well as combinations thereof.

"Stretchable", refers to materials which are either elastic or extensible, that is materials which when elongated in one or more dimensions either exert a force tending to move the material at least partially to its original dimensions (elastic), or which remain in the elongated configuration (extensible).

It should be noted that the stretch, elastic or extensible properties of a stretchable material are determined when the material is dry. Additionally, the percentage of elongation, extension or permanent deformation can be determined in accordance with the following formula:

$$100*[(L-L_o)/(L_o)]$$

where:

$L$=elongated length; and $L_o$=initial length.

Figure 1:
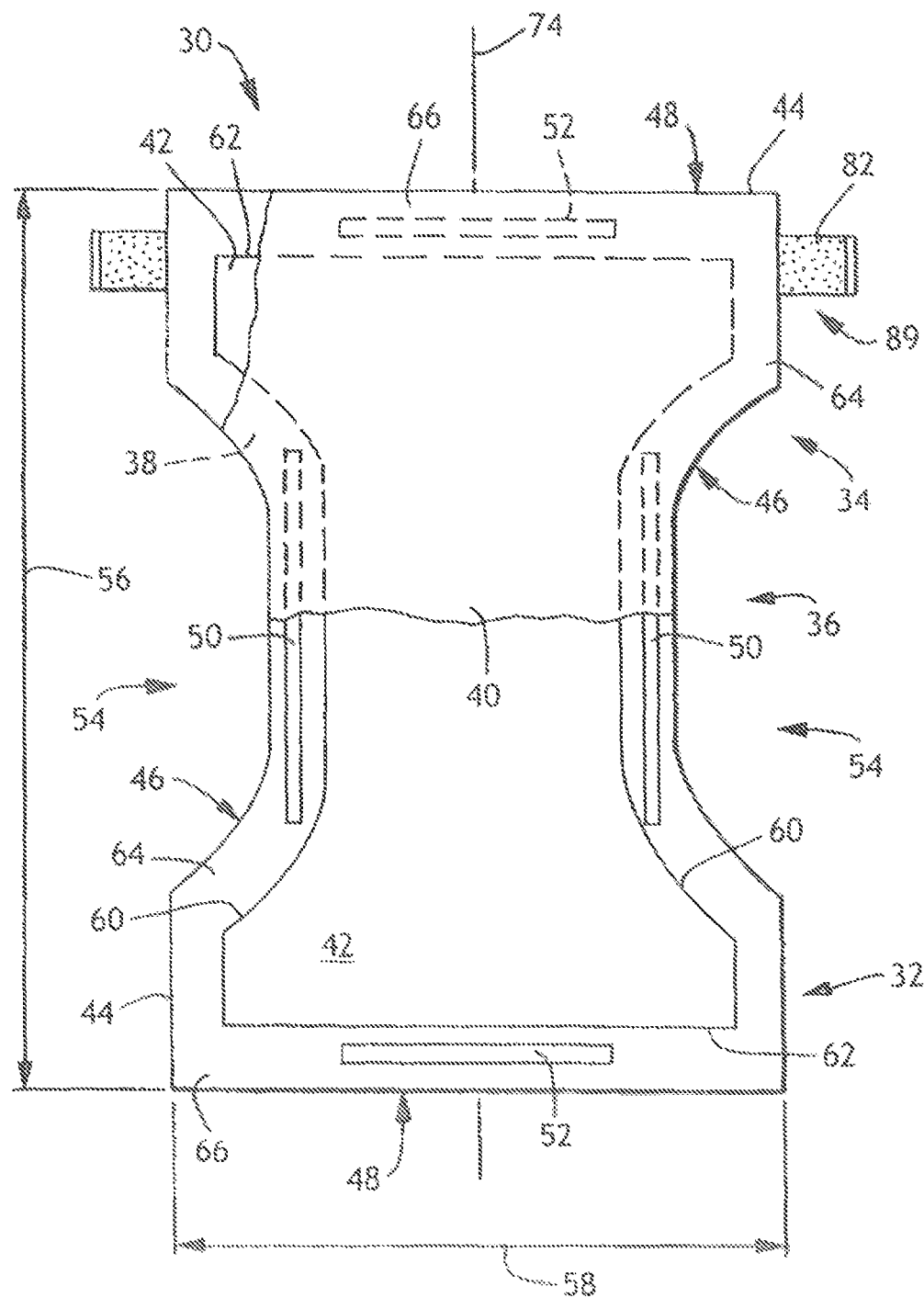
FIG. 1 illustrates a plan view of a disposable absorbent article in an unfolded, flat-out, uncontracted state (i.e., with all elastic induced gathering and contraction removed), with the bodyfacing surface of the article facing the viewer and with portions of the article partially cut away to illustrate underlying features.
Figure 2:
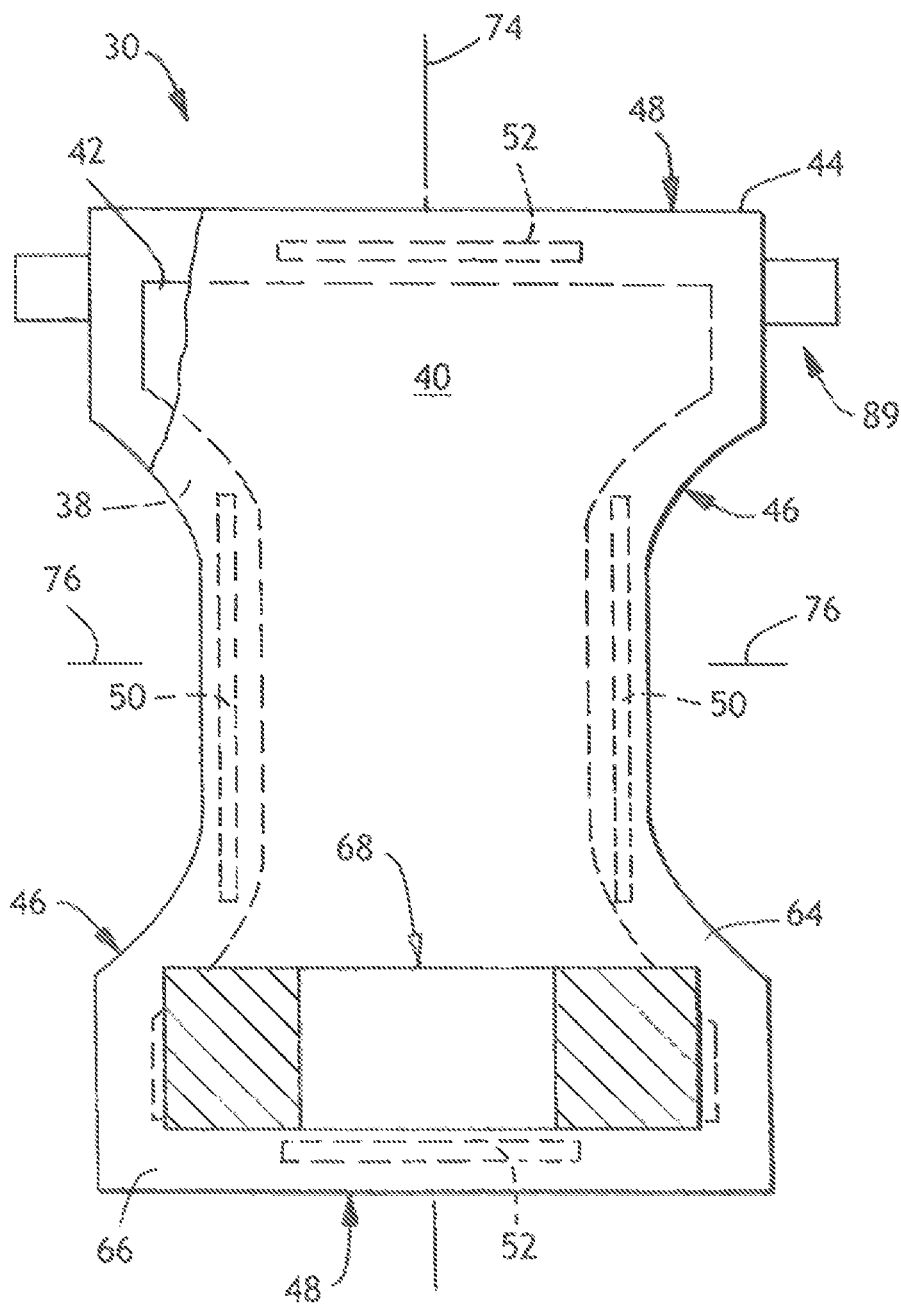
FIG. 2 illustrates a plan view of a disposable absorbent article in an unfolded, flat-out, uncontracted state, with the garment facing surface of the article facing the viewer and with portions of the article partially cut away to illustrate underlying features with a modified area of a female component.

Referring now to the drawings, FIG. 1 illustrates a disposable absorbent article such as a disposable diaper (30) in an unfolded, flat-out, uncontracted state (i.e., with all elastic induced gathering and contraction removed). Portions of the structure are partially cut away to more clearly show the interior construction of the diaper (30), with the surface of the diaper (30) which contacts the wearer facing the viewer. FIGS. 1 and 2 illustrate a disposable diaper (30) as having a front region (32), a rear region (34) and a crotch portion (36) located between the front and rear regions. The diaper (30) comprises a backsheet (38), a topsheet (40), and an absorbent core (42) situated between the backsheet and the topsheet. The outer edges of the diaper (30) define a periphery (44) with transversely opposed, longitudinally extending side edges (46); longitudinally opposed, transversely extending end edges (48); and a system of elastomeric gathering members, such as a system including leg elastics (50) and waist elastics (52). The longitudinal side edges (46) define the leg openings (54) for the diaper (30), and optionally, are curvilinear and contoured. The transverse end edges (48) are illustrated as straight, but optionally, may be curvilinear. The diaper (30) may also comprise additional components to assist in the acquisition, distribution and storage of bodily waste. For example, the diaper (30) may comprise a transport layer, such as described in U.S. Pat. No. 4,798,603, issued to Meyer et al., or a surge management layer, such as described in European Patent Application Publication No. 0 539 703, published May 5, 1993.

The diaper (30) generally defines a longitudinally extending length dimension (56), and a laterally extending width dimension (58), as representatively illustrated in FIG. 1. The diaper (30) may have any desired shape, such as rectangular, I-shaped, a generally hourglass shape, or a T-shape. The backsheet (38) defines a length and a width which, in the illustrated version, coincide with the length and width of the diaper (30). The absorbent core (42) generally defines a length and width which are less than the length and width of the backsheet (38), respectively. Thus, marginal portions of the diaper (30), such as marginal sections of the backsheet (38), may extend past the transversely opposed, longitudinally extending terminal side edges (60) and/or the longitudinally opposed, transversely extending terminal end edges (62) of the absorbent core (42) to form side margins (64) and end margins (66) of the diaper (30). The topsheet (40) is generally coextensive with the backsheet (38), but may optionally cover an area which is larger or smaller than the area of the backsheet, as desired. The backsheet (38) and topsheet (40) are intended to face the garment and body of the wearer, respectively, while in use. As used herein when describing the topsheet (40) in relation to the backsheet (38) and vice versa, the term "associated" encompasses configurations in which the topsheet is directly joined to the backsheet, and configurations where the topsheet is indirectly joined to the backsheet by affixing portions of the topsheet to intermediate members which in turn are affixed to at least portions of the backsheet. The topsheet (40) and the backsheet (38) can, for example, be joined to each other in at least a portion of the diaper periphery (44) by attachment mechanisms (not shown) such as adhesive bonds, sonic bonds, thermal bonds, pinning, stitching, or a variety of other attachment techniques known in the art, as well as combinations thereof.

The topsheet (40) suitably presents a bodyfacing surface which is compliant, soft feeling, and non-irritating to the wearer's skin. Further, the topsheet (40) may be less hydrophilic than the absorbent core (42), to present a relatively dry surface to the wearer, and is sufficiently porous to be liquid permeable, permitting liquid to readily penetrate through its thickness. A suitable topsheet (40) may be manufactured from a wide selection of web materials, such as porous foams, reticulated foams, apertured plastic films, natural fibers, synthetic fibers (for example, polyester or polypropylene fibers), or a combination of natural and synthetic fibers. The topsheet (40) is suitably employed to help isolate the wearer's skin from liquids held in the absorbent core (42).

Various woven and nonwoven fabrics may be used for the topsheet (40). For example, the topsheet (40) may be composed of a meltblown or spunbonded web of polyolefin fibers. The topsheet (40) may also be a bonded-carded web composed of natural and/or synthetic fibers. The topsheet (40) may be composed of a substantially hydrophobic material, and the hydrophobic material may, optionally, be treated with a surfactant, or otherwise processed, to impart a desired level of wettability and hydrophilicity. Specifically, the topsheet (40) may be a nonwoven, spunbond, polypropylene fabric composed of about 2.8 to about 3.2 denier fibers formed into a web having a basis weight of about 22 gsm and a density of about 0.06 g/cc.

The topsheet (40) may also be surface treated with about 0.3 weight percent of a surfactant mixture that contains a mixture of AHCOVEL Base N-62 surfactant and GLUCOPON 220UP surfactant in about a 3:1 ratio based on a total weight of the surfactant mixture. The AHCOVEL Base N-62 surfactant is purchased from Hodgson Textile Chemicals Inc., a business having offices in Mount Holly, N.C., and comprises a blend of hydrogenated ethoxylated castor oil and sorbitan monooleate in a 55:45 weight ratio. The GLUCOPON 220UP surfactant is purchased from Henkel Corporation, Gulph Mills, Pa., and comprises alkyl polyglycoside. The surfactant may also include additional ingredients such as aloe. The surfactant may be applied by any conventional means, such as spraying, printing, brush coating, foam or the like. The surfactant may be applied to the entire topsheet (40) or may be selectively applied to particular sections of the topsheet, such as the medial section along the longitudinal centerline of a diaper, to provide greater wettability of such sections.

The backsheet (38) may suitably be composed of a material which is either liquid permeable or liquid impermeable. It is generally desirable that the backsheet (38) be formed from a material which is substantially liquid impermeable. For example, a typical backsheet (38) can be manufactured from a thin plastic film or other flexible liquid impermeable material. Moreover, the backsheet (38) may be formed from a polyethylene film having a thickness of from about 0.012 mm (0.5 mil) to about 0.051 mm (2.0 mils). If desirous of presenting the backsheet (38) with a more cloth-like feel, the backsheet may comprise a polyethylene film having laminated to the lower or opposing surface thereof a nonwoven web, such as a spunbond web of polyolefin fibers. For example, a polyethylene film having a thickness of about 0.015 mm (0.6 mil) may have thermally laminated thereto a spunbond web of polyolefin fibers, which fibers have a thickness of about 1.5 to about 2.5 denier per filament, which nonwoven web has a basis weight of about 24 gsm (0.7 osy). Methods of forming such cloth-like outer covers are known to those skilled in the art. Further the backsheet (38) may be a stretchable material, a method of forming such a material may be found in U.S. Pat. No. 5,226,992 issued to Morman, further various examples of extensible materials are described in U.S. Pat. No. 6,264,641 issued to VanGompel et al.; the entire disclosures of which are hereby incorporated by reference in a manner that is consistent herewith Further, the backsheet (38) may be formed of a woven or nonwoven fibrous web layer which has been totally or partially constructed or treated to impart a desired level of liquid impermeability to selected regions that are adjacent or proximate the absorbent core (42). Still further, the backsheet (38) may optionally be composed of micro-porous "breathable" material which permits vapors to escape from the absorbent core (42) while still preventing liquid exudates from passing through the backsheet.

The absorbent core (42) may comprise a matrix of hydrophilic fibers, such as a web of cellulosic fluff, mixed with particles of a high-absorbency material commonly known as superabsorbent material. In a particular version, the absorbent core (42) comprises a mixture of superabsorbent hydrogel-forming particles and wood pulp fluff. The wood pulp fluff may be exchanged with synthetic polymeric, meltblown fibers or with a combination of meltblown fibers and natural fibers. The superabsorbent particles may be substantially homogeneously mixed with the hydrophilic fibers or may be non-uniformly mixed.

The absorbent core (42) may have any of a number of shapes. For example, the absorbent core (42) may be rectangular, 1-shaped or T-shaped. It is often considered as desirable for the absorbent core (42) to be narrower in the crotch portion than the rear or front region(s).

The high-absorbency material can be selected from natural, synthetic and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble, but swellable. Such means can comprise, for example, physical entanglement, crystalline domains, covalent bonds, ionic complexes and associations, hydrophilic associations, such as hydrogen bonding, and hydrophobic associations or Van der Waals forces.

Examples of synthetic, polymeric, high-absorbency materials include the alkali metal and ammonium salts of poly (acrylic acid) and poly(methacrylic acid), poly(acrylamides), poly(vinyl ethers), maleic anhydride copolymers with vinyl ethers and alpha-olefins, poly(vinyl pyrolidone), poly (vinyl morpholinone), poly(vinyl alcohol), and mixtures and copolymers thereof. Further polymers suitable for use in the absorbent core include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthum gum, locust bean gum, and the like. Mixtures of natural and wholly or partially synthetic absorbent polymers can also be useful. Processes for preparing synthetic, absorbent gelling polymers are disclosed in U.S. Pat. No. 4,076,663, issued to Masuda et al., and U.S. Pat. No. 4,286,082, issued to Tsubakimoto et al.

The high-absorbency material may be in a variety of geometric forms. It is desired that the high-absorbency material be in the form of discrete particles. However, the high-absorbency material may also be in the form of fibers, flakes, rods, spheres, needles, or the like. Often, the high-absorbency material is present in the absorbent core (42) in an amount of from about 5 to about 100 weight percent based on total weight of the absorbent core.

The disposable absorbent articles described herein also comprise fasteners (82) for securing the absorbent article about the waist of the wearer. The illustrated versions of the diaper (30) comprise such fasteners (82). In at least one version, the fasteners (82) are situated in the rear region (34) of the diaper (30), and located inboard each longitudinal extending side edge (46). The fasteners (82) may be configured to encircle the hips of the wearer and engage the backsheet (38) of the front region (32) of the diaper (30) for holding the diaper (30) on the wearer. Suitable fasteners are well known to those of skill in the art and can comprise adhesive tape tab fasteners, hook and loop fasteners, mushroom fasteners, snaps, pin, belts and the like, and combinations thereof. Desirably, the fasteners (82) are releasably engageable directly with the garment facing surface of the backsheet (38). Desirably, the fasteners (82) comprise a mechanical fastening system. Alternatively, the diaper (30) may comprise a fastening panel (68) situated in the front region (32) of the garment facing surface of the backsheet (38). In such a configuration, the fasteners (82) are releasably engageable with the fastening panel (68) to maintain the diaper (30) about the waist of the wearer. Such an arrangement provides the ability to vary the size of the waist opening in very small increments over a wide range to fit the waist of the wearer. The fasteners (82) may have a variety of shapes and sizes which provide the desired fastening of the diaper (30) about the waist of the wearer.

Desirably, the first fastener component and cooperating fastener component comprise complementary elements of a cooperatively interengaging mechanical fastening system. The mechanical fastener components can be provided by mechanical-type fasteners such as hooks, buckles, snaps, buttons and the like, which comprise cooperating and complementary, mechanically interlocking components.

As shown in FIGS. 1 and 2, for example, the mechanical fastening system may be a hook-and-loop type of fastening system. Such fastening systems typically comprise engagement members having the form of a "hook" or hook-like, male component, and comprise a cooperating "loop" or loop-like, female component, which engages and releasably interconnects with the hook component. Desirably, the interconnection is selectively releasable and re-attachable. Conventional systems are, for example, available under the VELCRO trademark.

A configuration which employs a selectively releasable, inter-engaging mechanical fastening system can, for example, locate the first fastener component on the ear (89), and can locate the cooperating, second fastener component on the fastening panel (68). For example, with the representatively shown hook-and-loop fastener, the fastening component, which is attached to the ear (89), may comprise a hook type of mechanical engagement element, and the complementary fastening component, is the fastening panel (68) which can comprise a loop type of fastening element.

It should also be readily apparent that, in the various configurations of the invention, the relative positions and/or materials of the first fastening component and its cooperating, complementary fastening component can be transposed.

Examples of hook-and-loop fastening systems and components are described in U.S. Pat. No. 5,019,073 issued to Roessler et al, the entire disclosure of which is hereby incorporated by reference in a manner that is consistent herewith. Other examples of hook-and-loop fastening systems are described in U.S. Pat. Nos. 5,605,735 and 6,030,373 issued to VanGompel et al.; the entire disclosures of which are hereby incorporated by reference in a manner that is consistent herewith. Examples of fastening tabs constructed with a carrier layer are described in U.S. Pat. No. 5,624,429 issued to Long et al., the entire disclosure of which is hereby incorporated by reference in a manner which is consistent herewith.

The loop material can comprise a nonwoven, woven or knit fabric. For example, a suitable loop material fabric can be composed of a 2 bar, warp knit fabric of the type available from Guilford Mills, Inc., Greensboro, N.C. under the trade designation #34285, as well as other types of knit fabrics. Suitable loop materials are also available from the 3M Company, which has distributed a nylon woven loop under their SCOTCHMATE brand. The 3M Company has also distributed a linerless loop web with adhesive on the backside of the web, and 3M knitted loop tape.

The loop material may also comprise a nonwoven fabric having continuous bonded areas defining a plurality of discrete unbonded areas. The fibers or filaments within the discrete unbonded areas of the fabric are dimensionally stabilized by the continuous bonded areas that encircle or surround each unbonded area, such that no support or backing layer of film or adhesive is required. The unbonded areas are specifically designed to afford spaces between fibers or filaments within the unbonded area that remain sufficiently open or large to receive and engage hook elements of the complementary hook material. In particular, a pattern-unbonded nonwoven fabric or web may comprise a spunbond nonwoven web formed of single component or multi-component melt-spun filaments. At least one surface of the nonwoven fabric can comprise a plurality of discrete, unbonded areas surrounded or encircled by continuous bonded areas. The continuous bonded areas dimensionally stabilize the fibers or filaments forming the nonwoven web by bonding or fusing together the portions of the fibers or filaments that extend outside of the unbonded areas into the bonded areas, while leaving the fibers or filaments within the unbonded areas substantially free of bonding or fusing. The degree of bonding or fusing within the bonding areas desirably is sufficient to render the nonwoven web non-fibrous within the bonded areas, leaving the fibers or filaments within the unbonded areas to act as "loops" for receiving and engaging hook elements. Examples of unmodified, suitable point-unbonded fabrics are described in U.S. Pat. No. 5,858,515, issued to by Stokes et al., the entire disclosure of which is incorporated herein by reference in a manner that is consistent herewith.

As used herein, the term "spunbond web" refers to a web formed by extruding a molten thermoplastic material as filaments from a plurality of fine, usually circular, capillaries with the diameter of the extruded filaments then being rapidly reduced, for example, by fluid-drawing or other well known spunbonding mechanisms. The production of spunbond nonwoven webs is illustrated in U.S. Pat. No. 4,340,563, issued to Appel, et al., the entire disclosure of which is incorporated herein by reference in a manner that is consistent herewith.

The loop material need not be limited to a discrete or isolated patch on the outward surface of the article. Instead, the loop material can be provided by a substantially continuous, outer fibrous layer which is assembled, integrated or otherwise joined to extend over a predetermined surface area of the desired article. For example, the outer fibrous layer may be arranged to extend over substantially the total exposed surface area of a cloth-like outer cover employed with the article. Further, the outer cover can comprise an outer nonwoven layer that functions as a cooperating fastener component.

The engagement force between the selected first fastener component and its appointed and cooperating second fastener component should be large enough and durable enough to provide an adequate securement of the article on the wearer during use. In particular arrangements, especially where there are sufficiently high levels of engagement shear force provided by the fastening system, the fastening engagement may provide a peel force value of not less than a minimum of about 40 grams-force (gmf) per inch of the "width" of engagement between the first and second fastener components. In further arrangements, the fastening engagement may provide a peel force value of not less than about 100 gmf/inch to provide improved advantages. In desired configurations, the fastening engagement may provide a peel force value of not less than about 200 gmf per inch of the "width" of engagement between the first and second fastener components. Alternatively, the peel force is not less than about 300 gmf/inch, and optionally is not less than about 400 gmf/inch to further provide improved benefits. In other aspects, the peel force is not more than about 1,200 gmf/inch. Alternatively, the peel force is not more than about 800 gmf/inch, and optionally is not more than about 600 gmf/inch to provide improved performance.

The engagement force between the selected first fastener component and its appointed and cooperating second fastener component may additionally provide a shear value of not less than about 400 gmf per square inch of the area of engagement between the first and second fastener components. Alternatively, the shear force is not less than about 1,000 $gmf/in^2$, and optionally, is not less than about 1,700 $gmf/in^2$. In further aspects, the shear force can be up to about 4,400 $gmf/in^2$, or more. Alternatively, the shear force is not more than about 3,900 $gmf/in^2$, and optionally is not more than about 3,500 $gmf/in^2$ to provide improved performance.

The engagement force between a given male component and a given female component may be changed by selective modification of the female component. Further, by selectively modifying a portion of the female component, a first area and a second area may be formed, the first area being modified, and the second are being unmodified. A reduction of engagement force may be achieved by printing with wax-based inks. As the examples described hereinafter show, printing with wax based inks reduces the shear force required to separate the male and female components. While not to be bound by any theory, but it is believed that the reduction of engagement is caused by the wax based inks interfering with the ability of the male component to engage the female component. An advantage of this selective modification of the female component is that a given base material with a given engagement force may be modified to reduce the engagement force by a lesser or greater degree. This may be highly advantageous where the female component has been designed to be very soft and cloth-like and thereby susceptible to abrasion by the male component. By reducing the engagement force, the female component may remain soft and cloth-like while improving its abrasion resistance. This reduction of engagement may be accomplished in at least two ways. First, the reduction of engagement may be increased or decreased by modifying the amount of add-on of ink (the amount of ink applied per unit area). Within ranges, an increase of ink add-on will increase the reduction of engagement, and a decrease of ink add-on will decrease the reduction of engagement. In addition to ink, that female component may be coated with a number of materials, for example high melt flow polymers, mPE, MPP, hot melt adhesives, APAO, elastomeric olefinics, non-tacky polymers or other suitable polymeric material, or combinations of the aforementioned. In addition to printing, any one or combinations of the above may be applied to the female component by misting, spraying, streaking, or slot coating.

A second way to adjust the level of reduction of engagement is to modify the area that is treated, on a micro scale. For example, instead of printing the material with a uniform layer of ink, the material can be printed with small dots or lines, such that, there are printed areas, and un-printed areas. Material may be printed such that there is more or less coverage in a given area. In this way, the amount of reduction of engagement can be "adjusted", by increasing the area printed, approaching complete coverage to achieve the reduction of engagement of complete coverage, or decreasing the area printed, approaching no coverage to achieve no reduction.

A second method used to modify the engagement of a given female component is embossing. While not to be bound by any theory, but it is believed that the reduction of engagement is caused by the embossing interfering with the ability of the male component to engaging the female component. Embossing takes place when a material comes in contact with a surface and energy is transferred from the surface to the material which in some way permanently modifies the material. This surface may be a roller, a flat anvil or alternatively, it may be two rollers that form a nip. The energy may be in the form of pressure, thermal, ultrasonic or other suitable form, or combinations of these forms. As with the method of printing, the reduction of engagement may be increased or decreased in at least two ways. First, the reduction of engagement may be increased or decreased by modifying the level of embossing. Within ranges, the level of embossing may be increased by increasing the amount of energy that is transferred from the surface to the material. For instance, with thermal embossing, one way to increase the level of embossing may be to increase the temperature of the embossing surface. Correspondingly, reducing the temperature of the embossing surface may result in a decrease in the level of embossing. An increase in the level of embossing may increase the reduction of engagement, and a decrease in the level of embossing may decrease the reduction of engagement.

A second way the reduction of engagement may be increased or decreased is by use of a micro-scale embossing pattern. As with printing, an embossing pattern may have a smaller bond area, which may correspond with a lower reduction of engagement; alternatively, an embossing pattern may have a larger bond area, which may correspond with a higher reduction of engagement. Embossing patterns with different bond areas are well known in the art.

The reduction of engagement is determined by measuring the engagement force of the un-modified area ($F_0$), and the engagement force of the modified area ($F_1$). The equation for the percent reduction of engagement is $100*[(F_0-F_1)/(F_0)]$.

The difference between the engagement between the modified (first area) and unmodified area (second area) may be increased or decreased by the methods described above. Desirably, the reduction of engagement is no less than 5%; alternatively, no less than 10%; alternatively, no less than 15%; alternatively, no less than 22%; alternatively, no less than 30%; alternatively, no less than 37%; alternatively, no less than 45%; alternatively, no less than 49%; alternatively, no less than 54%; alternatively, no less than 60% and finally, alternatively, no less than 70%. Desirably, the reduction of engagement is no more than 65%; alternatively, no more than 58%; alternatively, no more than 52%; alternatively, no more than 45%; alternatively, no more than 39%; alternatively, no more than 33%; alternatively, no more than 29%; alternatively, no more than 24%; alternatively, no more than 21%; alternatively, no more than 18%; alternatively, no more than 14%; alternatively, no more than 11%; and finally, alternatively, no more than 5%. Thus, the reduction of engagement is no less than 5% and no more than 70%; although the approximate percent may vary according to, inter alia, the general design and intended use of the female fastener.

Desirably, the percentage of the area of the female component that is modified to reduce engagement is no less then 1; alternatively, no less than 6; alternatively, no less than 13; alternatively, no less than 15; alternatively, no less than 19; alternatively, no less than 25; alternatively, no less than 27; alternatively, no less than 33; alternatively, no less than 36; alternatively, no less than 41; alternatively, no less than 45; alternatively, no less than 47; alternatively, no less than 52; alternatively, no less than 55; alternatively, no less than 61; alternatively, no less than 63; alternatively, no less than 68; alternatively, no less than 71; alternatively, no less than 77; alternatively, no less than 81; alternatively, no less than 83; alternatively, no less than 87; alternatively, no less than 92; alternatively, no less than 97; and finally, alternatively, no less than 98. Desirably, the percentage of the area of the female component that is modified to reduce engagement is no more than 99; alternatively, no more than 96; alternatively, no more than 91; alternatively, no more than 88; alternatively, no more than 82; alternatively, no more than 81; alternatively, no more than 76; alternatively, no more than 72; alternatively, no more than 68; alternatively, no more than 63; alternatively, no more than 60; alternatively, no more than 55; alternatively, no more than 51; alternatively, no more than 48; alternatively, no more than 45; alternatively, no more than 40; alternatively, no more than 37; alternatively, no more than 33; alternatively, no more than 27; alternatively, no more than 25; alternatively, no more than 19; alternatively, no more than 14; alternatively, no more than 12; alternatively, no more than 7; and finally, alternatively, no more than 5. Thus, the percentage of the area of the female component that is modified to reduce engagement typically is no less than 1% and no more than 99%; although the approximate percent may vary according to, inter alia, the general design and intended use of the female fastener.

The female component may be a point-unbonded fabric as described in U.S. Pat. No. 5,858,515, issued to by Stokes et al, and further as found as a fastening panel (68) on commercially available HUGGIES ULTRATRIM diapers. Alternatively, the female component may be a stretchable material, a method of forming such a material may be found in U.S. Pat. No. 5,226,992 issued to Morman, further various examples of suitable materials are described in U.S. Pat. No. 6,264,641 issued to VanGompel et al.

In desired configurations, the female component can provide a stretch elongation as measured at 250 g/in. Desirably the female component can provide a stretch elongation that is no less than 3%, alternatively, no less than 5% of the backsheet area; alternatively, no less than 10% of the backsheet area; alternatively, no less than 15% of the backsheet area; and finally, alternatively, no less than 20%. Desirably the female component can provide a stretch elongation measure at 250 g/in that is no more than 30%; alternatively, no more than 25%; alternatively, no more than 20%; alternatively, no more than 15%; and finally, alternatively, no more than 10%. Thus, the female component typically can provide a stretch elongation measured at 250 g/in that is no less than 3% and no more than 30%; although the approximate percent may vary according to, inter alia, the general design and intended use of the female component.

The female component may form the backsheet. Alternatively, the female component may be attached to the backsheet (38). Desirably, the area of the female component is no less than 1% of the back sheet area; alternatively, no less than 9% of the backsheet area; alternatively, no less than 18% of the backsheet area; alternatively, no less than 27% of the backsheet area; alternatively, no less than 36% of the backsheet area; alternatively, no less than 45% of the backsheet area; alternatively, no less than 52% of the backsheet area; alternatively, no less than 61% of the backsheet area; alternatively, no less than 68% of the backsheet area; alternatively, no less than 77% of the backsheet area; alternatively, no less than 83% of the backsheet area; alternatively, no less than 92% of the backsheet area; and finally, alternatively, no less than 98% of the backsheet area. Desirably, the area of the female component is no more than 100% of the backsheet area; alternatively, no more than 91% of the backsheet area; alternatively, no more than 82% of the backsheet area; alternatively, no more than 76% of the backsheet area; alternatively, no more than 68% of the backsheet area; alternatively, no more than 60% of the backsheet area; alternatively, no more than 51% of the backsheet area; alternatively, no more than 45% of the backsheet area; alternatively, no more than 37% of the backsheet area; alternatively, no more than 27% of the backsheet area; alternatively, no more than 19% of the backsheet area; alternatively, no more than 12% of the backsheet area; and finally, alternatively, no more than 5% of the backsheet area. Thus, the area of the female component typically is no less than 1% and no more than 100% of the backsheet area; although the approximate percent may vary according to, inter alia, the general design and intended use of the female component.

Figure 3:
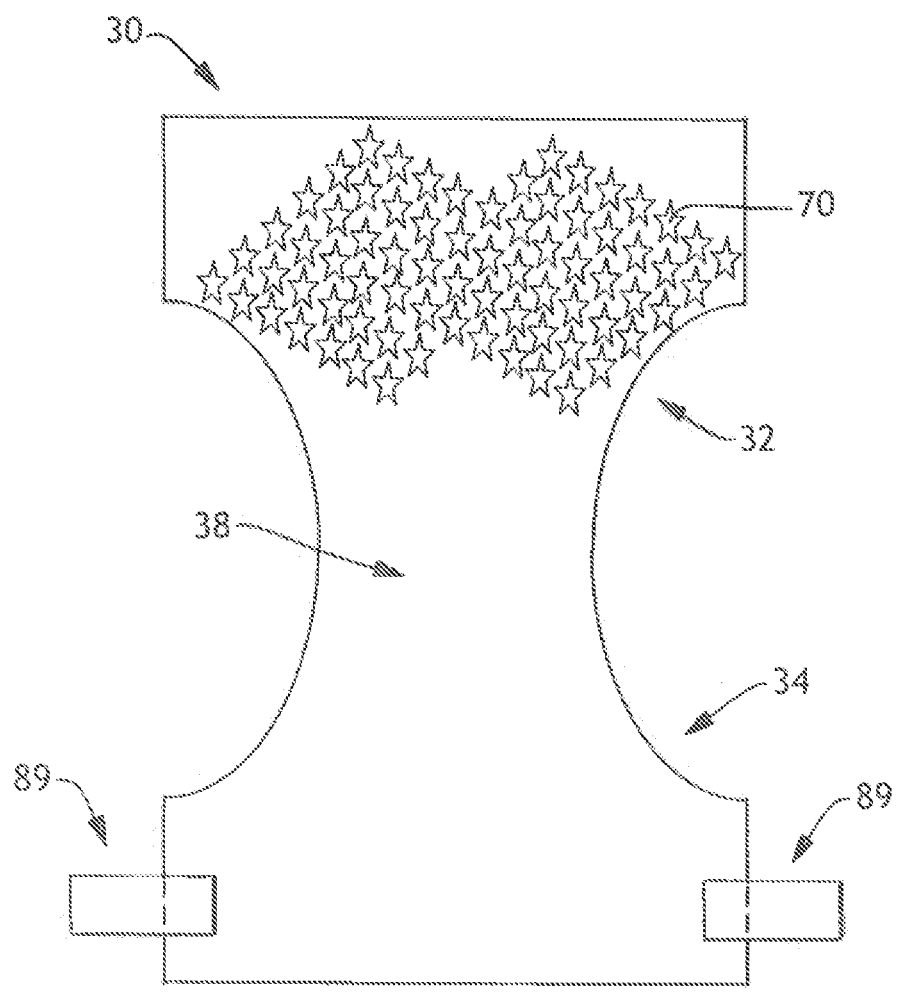
FIG. 3 illustrates a plan view of a disposable absorbent article in an unfolded, flat-out, uncontracted state, with the garment facing surface of the article facing the viewer with a modified area of a female component.
Figure 4:
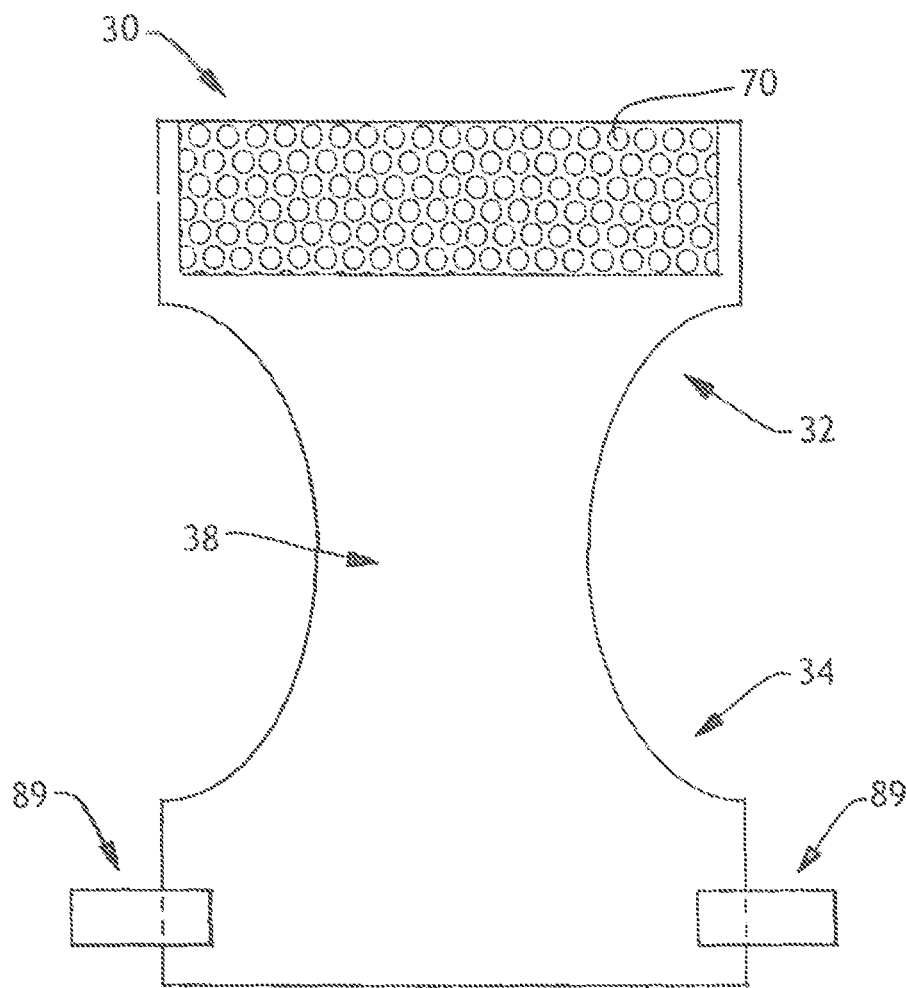
FIG. 4 illustrates a plan view of a disposable absorbent article in an unfolded, flat-out, uncontracted state, with the garment facing surface of the article facing the viewer with a modified area of a female component.

As shown in FIGS. 3 and 4, the modified area (70) of the female component may be shaped and positioned in many ways. FIG. 3 illustrates a diaper having an outer cover comprising a nonwoven web. The nonwoven web functions as a female fastening component, with a first region and second region. The first region is defined by coverage of printing or embossing denoted by a plurality of star-shaped elements. FIG. 4 illustrates a diaper having an outer cover comprising a nonwoven web. The nonwoven web functions as a female fastening component, with a first region and second region. The first region is defined by coverage of printing or embossing denoted by a plurality of circular shaped elements. With regard to the location of the first region, on a diaper (30) with fasteners (82) located in the rear region (34), the area (70) of the female component that is modified may be located in the front region (32). Further, the area (70) of the female component that is modified may consist of a simple geometric shape such as a rectangle shown in FIG. 4. Alternatively, the area of the female component that is modified may consist of a more complex shape, such as a pattern of two overlapping diamonds shown in FIG. 3. The shape and size may vary according to the general design and intended use of the female component.

The shear strength of a mechanical fastening system can be determined in accordance with the following method.
Test Method: Shear Strength
Test Procedure This procedure is a tensile bench test to measure the shear force required to separate a mechanical fastening system that joins two materials. The shear force of separation is measured by determining load values as the two materials are pulled apart parallel to their plane of contact. The shear strength test values are an indication of how well the mechanical fastening system stays engaged against in-plane shear force. The sample is pulled in the tensile tester until the sample pulls apart. Shear strength is the peak load result. Shear strength may be normalized by dividing by the contact area resulting in a force per area.

1. Overview

A material sample of two material layers joined by a mechanical fastening system such as a hook and loop system is assembled. The fastening system joins two pieces of material that overlap in the landing area. The sample is prepared by aligning and applying the hook material to the loop material, and by rolling a 4.5 lb. (2.04 kg) mechanical roller over the fastening system to engage the fastener. The sample is then placed between clamps on a tensile tester. One piece of material is held in the upper clamp, while the other is held in the lower clamp. The fastening system is arrayed between the clamps, approximately parallel to the edges of the clamp faces. The width of the hook material is 13 mm, the width of the loop material is approximately 64 mm, and the hook overlaps the loop 50 mm. The gage length is 3 inches (76 mm) between the edges of the clamp faces. The term "load" refers to the gram value measured by the load cells in the tensile tester.

The jaws are separated at a controlled rate of 12 inch/min (305 mm/min until) the fastening system is pulled apart. The load values generated on the material throughout this process are recorded. The load as a function of elongation is recorded on a computer.

Load values for samples of non-standard widths and lengths should be normalized by multiplying or dividing by the factor by which the sample overlap area deviates from 13 mm by 50 mm. For example, the peak load value derived by pulling apart a 1 inch (25.4 mm) wide by 50 mm long sample should be multiplied by 13/25.4.

Suitable materials comprise hook and loop fastening systems, which may comprise or be attached to materials used to form the disposable garments described herein.

2. Apparatus and Materials 2.1 Constant Rate of Extension (CRE) tensile tester such as an MTS tensile tester model Sintech 1/G; available from MTS Systems Corporation, located at 1400 Technology Drive, Eden Prairie, Minn., USA.

2.2 Load cells: A suitable cell selected so the majority of the peak load values fall between 10% and 90% of the manufacturer's recommended ranges of load cell's full scale value; for example, Model 100N available from MTS Systems Corporation, located at 1400 Technology Drive, Eden Prairie, Minn., USA.

2.3 Operating software and data acquisition system such as MTS TestWorks® for Windows software version 3.10; available from MTS Systems Corporation, located at 1400 Technology Drive, Eden Prairie, Minn., USA.

2.4 Grips: pneumatic-action grips, top and bottom, identified as part number 38.00716 available from MTS Systems Corporation.

2.5 Grip faces: 25 by 75-mm (1 by 3-inch) interlocking faces such as are available from MTS Systems Corporation.

2.6 Roller: 4.5 lb (2.04 kg) mechanical roller available from Chemsultants International, Mentor, Ohio, USA.

3. Conditioning

Reasonable ambient conditions are required for testing. The instruments used should be calibrated as described in the manufacturer's instructions for each instrument.

Figure 5:
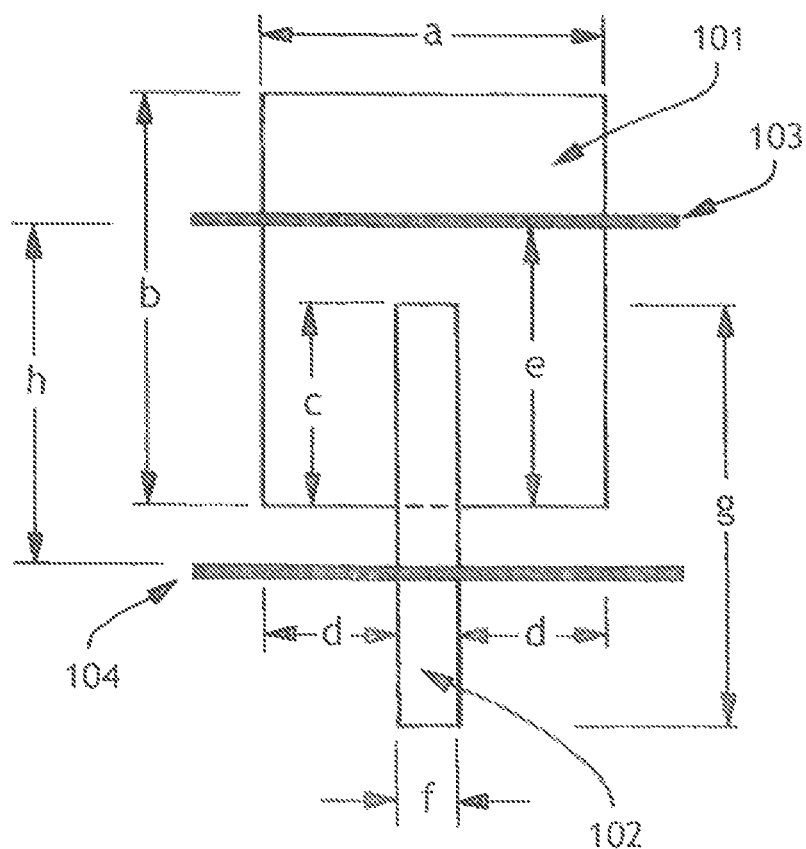
FIG. 5 illustrates a representative test sample.

4. Test Specimen (Illustrated in FIG. 5)

The loop material sample (101) is cut to have a width (a) of approximately 2.5 in. (64 mm) and a length (b) of approximately 4 in (102 mm). A hook material sample (102) having a width (f) of 13 mm and a length (g) of approximately 4 in. (102 mm) is placed onto the loop side of the loop material sample (101) such that the hook material sample (102) overlaps (c) the loop material sample (101) 50 mm, perpendicular from the 64 mm wide edge, centered on the 64 mm. The joined materials should not be handled or pressed.

The specimen is placed in a hard flat surface, and the test sample is then pressed down with a standard 4.5 lb (2.04 kg) mechanical roller by rolling the roller across the hook/loop engagement area back and forth in the length direction. The centerline of the sample should be aligned with the centerline of the face of the roller.

The specimen is tested using the tensile test procedure that follows. At least four specimens of each sample should be tested, and the results averaged.

5. Procedure

Tensile Tester Test Conditions

| Preload | No |
|---|---|
| Test speed | 305 mm/min |
| Gage length (h): | 3 inches (76 mm) |
| Number of cycles: | 1 |

A. Using the tensile frame pushbutton controls for crosshead position, move grips to provide a gage length (h) of 3 inches (76 mm). Tare the crosshead channel to this initial gage length.

B. Without touching the fastening area, hold a material specimen so that the loop material is up and the hook material is down. Place the loop material in the upper jaw (103) of the tester, such that loop material extends (e) below the lower edge of the upper jaw (103) 64 mm. Place the loop material in the upper jaw (103) such that it is centered in the horizontal direction, with the hook material extending below the center of the upper jaw (103).

C. Close the upper jaw (103) on the specimen and tare the load channel.

D. Hold the specimen in such a way as to minimize slack in the specimen, but do not place the specimen under tension, and close the lower jaw (104) on the hook material.

E. Run the test using the above parameters by clicking on the RUN button.

F. When the test is complete, save the data to a sample file.

G. Remove the specimen from the jaws (103, 104).

H. Run additional specimens of a given sample using steps B-G; the data for all specimens should be saved to a single file.

I. Continue testing all samples in this manner.

J. Data are reported as the peak load and the total energy under the load-extension curve.

The following examples were tested using the method described above, with noted deviations.

Examples

All Examples used Velcro HTH 851 male component with a 13 mm width.

Example One

Comparative Example

Two layer 1.5 total osy Point UnBonded spunbond. The top layer comprises 49% PP, 48.5% copoly, 1% OB and 1.5% TiO$_2$ with 27.1 micron fibers. The bottom layer comprises 97.5% PP, 1.5% OB and 1.0% TiO$_2$ with 24.9 micron fibers. The top layer comprises 60% of the web.

TABLE 1

Example 1

| Sample | Peak Load (g) | Total Energy (g-cm) |
|---|---|---|
| 1 | 3,717 | 7,791 |
| 2 | 4,185 | 10,294 |
| 3 | 4,284 | 10,456 |
| 4 | 3,513 | 6,857 |
| 5 | 4,085 | 8,164 |
| 6 | 4,179 | 10,652 |
| 7 | 4,319 | 10,961 |
| Average | 4,040 | 9,309 |

Example 2

Comparative Example

The material from Example 1 was printed using a MacDermid Color Span DispalyMaker Express Printer, 4 color CMYK.

Ink used: Hot-melt phase change wax inks (aka Wax-Jet inks)

DisplayMaker Express Ink Pucks

Ink drop size: 80 pico liters

Printer and inks available from MacDermid Color Span Corp., 6900 Shady Oak Road, Eden Prairie, Minn. 55444.

Results are shown in Table 2.

TABLE 2

Example 2

| Sample | Peak Load (g) | Total Energy (g-cm) |
|---|---|---|
| 1 | 1,972 | 3,793 |
| 2 | 2,762 | 5,748 |
| 3 | 2,159 | 3,945 |
| 4 | 3,372 | 5,890 |
| 5 | 3,224 | 5,899 |
| 6 | 1,982 | 3,779 |
| 7 | 2,219 | 4,003 |
| 8 | 2,828 | 5,208 |
| Average | 2,565 | 4,783 |

Example 3

Comparative Example

Three layer Neck bonded laminate. Top and bottom layer comprising 56% necked 0.85 osy Polypropylene Spunbond. The middle comprising 40 gsm Kraton G2755 film.

The material tested for examples 3 and 4 were 43 mm in width instead of the 64 mm of width for examples 1 and 2. This corresponds with dimension (a) from the test procedure. Further, the material sample was cut such that the stretch direction corresponded with the "b" dimension. Results are shown in Table 3.

TABLE 3

Example 3 (comparative example)

| Sample | Peak Load (g) | Total Energy (g-cm) |
|---|---|---|
| 1 | 1,042 | 4,387 |
| 2 | 1,291 | 4,335 |
| 3 | 1,392 | 5,987 |
| 4 | 1,404 | 6,242 |
| 5 | 1,186 | 4,646 |
| Average | 1,263 | 5,119 |

Example 4

Comparative Example

The material from Example 3 was ultrasonically bonded with a Branson 920 Plunge Bonder using a 13 mm horn and a flat anvil. The hold time was 3.00 seconds, the weld time was 3.00 seconds, the pressure was 500 kPa, and the trigger was 20. The area engaged by the hook material included only the portion of the material that was ultrasonically bonded.

Results are shown in Table 4.

TABLE 4

Example 4

| Sample | Peak Load (g) | Total Energy (g-cm) |
|---|---|---|
| 1 | 957 | 1,046 |
| 2 | 909 | 1,187 |
| 3 | 966 | 1,215 |
| 4 | 1,113 | 1,536 |
| Average | 986 | 1,246 |

A comparison of tables 1 and 2 indicates a reduction of engagement force of average peak load of 36.5 percent. Further, a comparison of tables 3 and 4 indicates a reduction of engagement force of 21.9 percent.

Having described the invention in rather full detail, it will be readily apparent that various changes and modifications can be made without departing from the spirit of the invention. All of such changes and modifications are contemplated as being within the scope of the invention as defined by the subjoined claims.

What is claimed is:

1. A disposable absorbent article comprising:
an outer cover having a bodyfacing surface and a garment facing surface;
a liner superposed over the bodyfacing surface of the outer cover, the outer cover comprising a substantially continuous outer cover nonwoven web;
an absorbent core disposed between the liner and the bodyfacing surface of the outer cover; and
a fastening system, the fastening system comprising a male component having a plurality of hook elements and a female component adapted for releasable engagement with the male component,
wherein the outer cover nonwoven web forms the female component, such that the male component is releasably engageable directly with the garment facing surface of the outer cover,
wherein the female component contains at least a first area and a second area, wherein the first area is modified by embossing a surface of the female component contacted by the male component, and wherein the first area comprises continuous bonded areas that define a plurality of discrete unbonded areas, wherein a peak shear force to disengage the male component from the first area is reduced by no less than 5% and no more than 70% of a peak shear force to disengage the male component from the second area.

2. The disposable absorbent article of claim 1, wherein the male component is located in a rear region of the disposable absorbent article, and the first area is located in a front region of the disposable absorbent article.

3. The disposable absorbent article of claim 1, wherein the peak shear force to disengage the male component from the first area is at least 20% less than the force to disengage the male component from the second area.

4. The disposable absorbent article of claim 1, wherein the first area is at least 10% of a total area of the female component.

5. The disposable absorbent article of claim 4, wherein the first area is at least 20% of the total area of the female component.

6. The disposable absorbent article of claim 4, wherein the first area is less than 80% of the total area of the female component.

7. The disposable absorbent article of claim 1, wherein the first area comprises a point-unbonded spunbond web in which each discrete unbonded area is surrounded by the continuous bonded areas.

8. A disposable absorbent article, the article having a bodyfacing surface and a garment facing surface, the article comprising:

a backsheet that comprises a substantially continuous nonwoven web, the backsheet including a bodyfacing surface and a garment facing surface;

an absorbent core disposed on the bodyfacing surface of the backsheet; and a fastening system comprising a male component disposed on the bodyfacing surface of the article, the male component adapted for direct releasable engagement with the garment facing surface of the backsheet, wherein the backsheet contains a first area and a second area, wherein the first area is modified by embossing a surface of the female component contacted by the male component, wherein the first area comprises continuous bonded areas that define a plurality of discrete unbonded areas, wherein a peak shear force to disengage the male component from the first area is reduced by no less than 5% and no more than 70% of a peak shear force to disengage the male component from the second area.

9. The disposable absorbent article of claim 8, wherein the male component is located in a rear region of the disposable absorbent article, and the first area is located in a front region of the disposable absorbent article.

10. The disposable absorbent article of claim 8, wherein the peak shear force to disengage the male component from the first area is at least 20% less than the force to disengage the male component from the second area.

11. The disposable absorbent article of claim 8, wherein the first area is at least 10% of a total area of the backsheet.

12. The disposable absorbent article of claim 11, wherein the first area is at least 20% of the total area of the backsheet.

13. The disposable absorbent article of claim 11, wherein the first area is less than 80% of the total area of the backsheet.

14. The disposable absorbent article of claim 8, wherein the first area comprises a point-unbonded spunbond web in which each discrete unbonded area is surrounded by the continuous bonded areas.

* * * * *